United States Patent [19]

Cupp et al.

[11] Patent Number: 4,892,518

[45] Date of Patent: Jan. 9, 1990

[54] HEMODIALYSIS

[75] Inventors: James R. Cupp, Indiana; Robert D. Norman, Clymer; David L. Purdy, Marion Center, all of Pa.; Orlando Maytin, Lauderdale Lakes, Fla.

[73] Assignee: Biocontrol Technology, Inc., Indiana, Pa.

[21] Appl. No.: 128,890

[22] Filed: Dec. 4, 1987

[51] Int. Cl.⁴ .......................................... A61M 11/00
[52] U.S. Cl. ...................................... 604/93; 604/175; 604/247; 604/173; 137/855
[58] Field of Search ................ 604/4, 5, 93, 175, 181, 604/183, 247, 256, 27, 36, 43, 9; 137/493, 855

[56]  References Cited

U.S. PATENT DOCUMENTS

| | | | |
|---|---|---|---|
| 3,070,089 | 12/1962 | Dick | 137/855 |
| 3,416,562 | 12/1968 | Freeman | 137/355 |
| 3,482,574 | 1/1987 | Stoever et al. | |
| 3,489,146 | 1/1967 | Rubin et al. | |
| 3,498,222 | 12/1976 | Shihata | 604/9 |
| 3,595,240 | 7/1971 | Mishler | 604/9 |
| 3,604,016 | 9/1971 | Robinson et al. | 3/1 |
| 3,685,059 | 8/1972 | Bokros et al. | 3/1 |
| 3,791,767 | 3/1972 | Shill | 417/389 |
| 3,826,257 | 6/1974 | Buselmeier | 604/8 |
| 3,882,862 | 5/1975 | Berend | 604/175 |
| 3,916,892 | 11/1975 | Latham, Jr. | |
| 4,014,328 | 3/1977 | Cluff et al. | 604/175 |
| 4,037,599 | 7/1977 | Raulerson | |
| 4,136,696 | 1/1979 | Nehring | 604/142 |
| 4,225,979 | 10/1980 | Rey et al. | 604/9 |
| 4,303,068 | 12/1981 | Zelman | 210/637 |
| 4,354,933 | 10/1982 | Lester | 210/251.2 |
| 4,417,888 | 11/1983 | Cosentino et al. | 604/175 |
| 4,428,745 | 1/1984 | Williams | 604/6 |
| 4,475,898 | 10/1984 | Brodner et al. | |
| 4,496,350 | 1/1985 | Cosentino | 604/175 |
| 4,535,786 | 8/1985 | Kater | 609/4 |
| 4,549,879 | 10/1985 | Groshong et al. | 604/9 |
| 4,643,711 | 2/1987 | Bates | 604/4 |
| 4,673,394 | 6/1987 | Fenten, Jr. et al. | 604/175 |
| 4,692,146 | 9/1987 | Hilger | 604/93 |
| 4,693,257 | 9/1987 | Markham | 604/198 |
| 4,704,103 | 11/1987 | Stöber et al. | 604/175 |
| 4,772,270 | 9/1988 | Wiita et al. | 604/175 |

Primary Examiner—C. Fred Rosenbaum
Assistant Examiner—Kathleen A. Daley
Attorney, Agent, or Firm—Hymen Diamond

[57]  ABSTRACT

Hemodialysis port assembly including a port and a catheter assembly. The port includes an inlet septum subtended by an inlet plenum and an outlet septum subtended by an outlet plenum. The catheter assembly includes an inlet channel connected to the inlet plenum and an outlet channel connected to the outlet plenum. The port and catheter assembly are completely implanted in the chest of a patient with the port subcutaneous and the end of the catheter assembly remote from the port injected into the subclavian vein. The blood flow in this vein is in the direction away from the end of the catheter assembly. Near this remote end the catheter assembly or the inlet channel terminates in an inlet valve and the outlet channel terminates in an outlet valve. Each of these valves is essentially a flapper on which the blood is incident in a generally perpendicular direction so that its flow is substantially unimpeded. The outlet valve is spaced a small but effective distance from the inlet valve in the downstream direction of the flow to toxified blood through the outlet channel. In practice of this invention, the detoxified blood from an artificial kidney is supplied to the vein through a hypodermic needle which penetrates the inlet septum, the inlet plenum, the inlet channel and the inlet valve and toxified blood is supplied from the vein to the artificial kidney through the outlet valve, the outlet channel, the outlet plenum and an outlet needle which penetrates the outlet septum. The spacing of the outlet valve from the inlet valve suppresses short-circuit flow of detoxified blood from the inlet branch to the outlet branch.

17 Claims, 7 Drawing Sheets

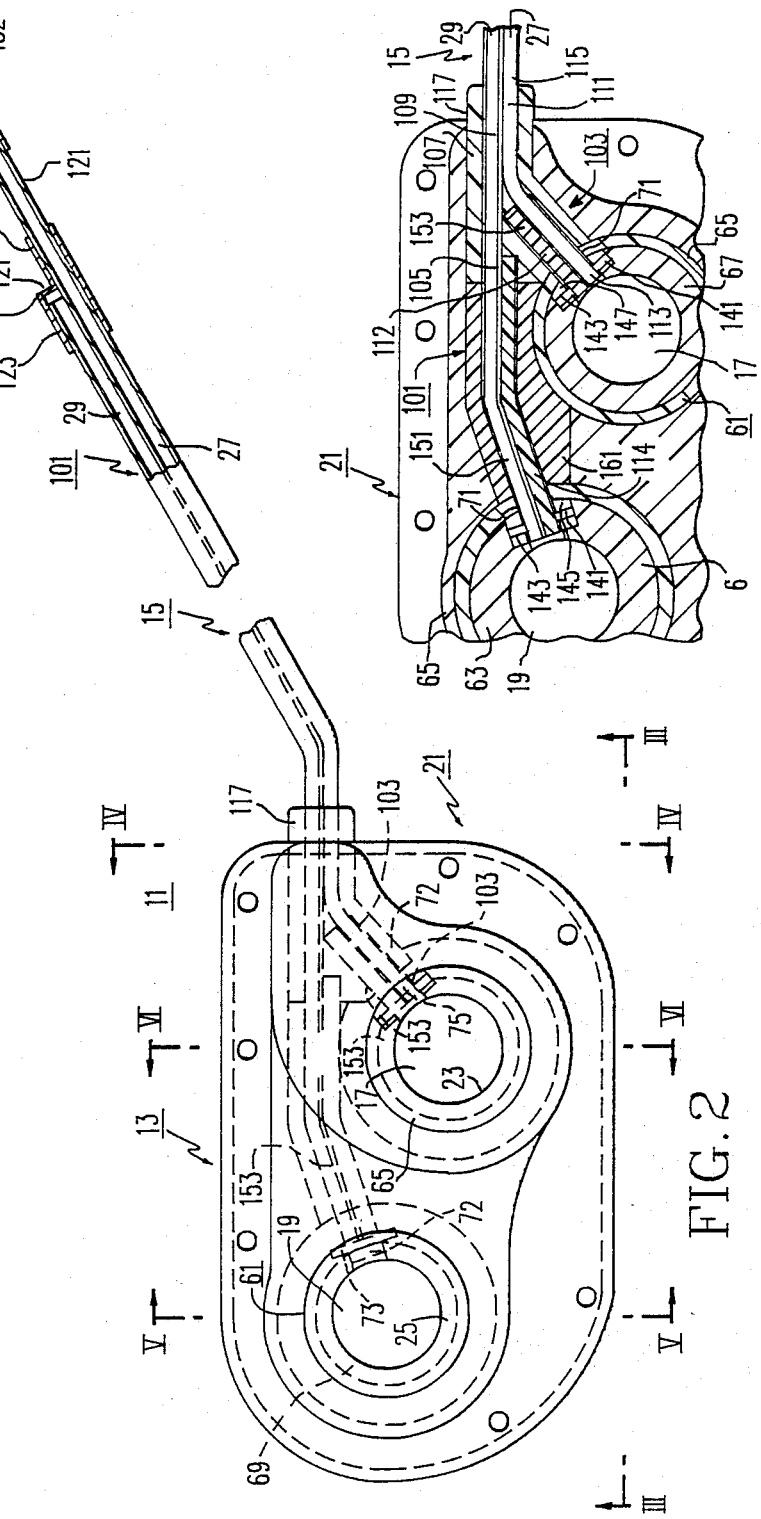

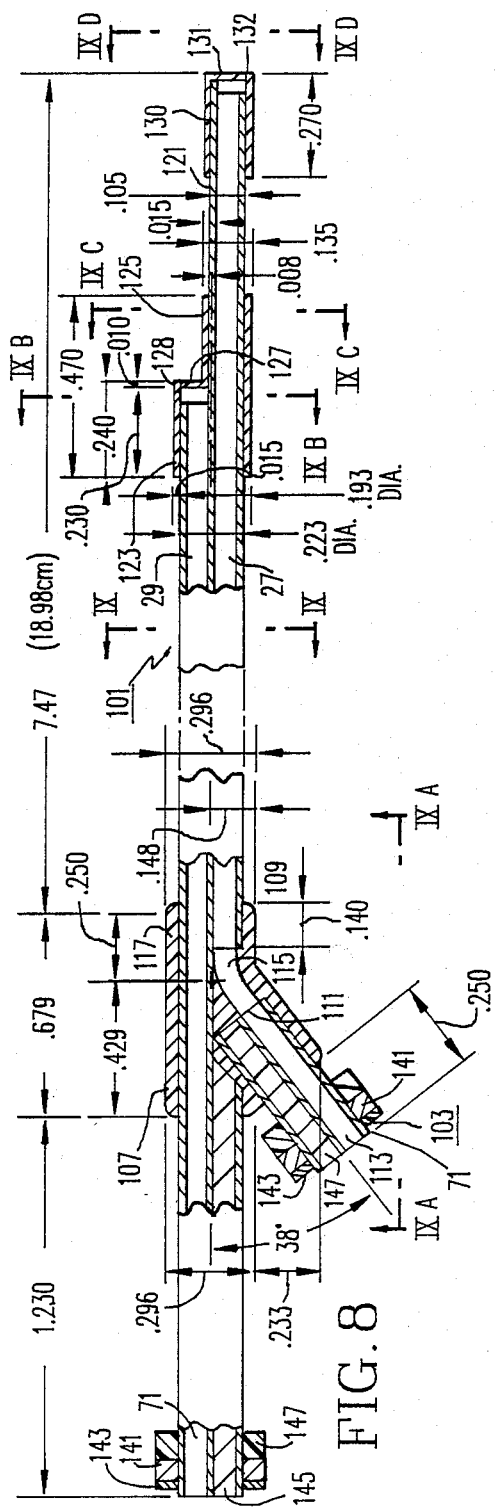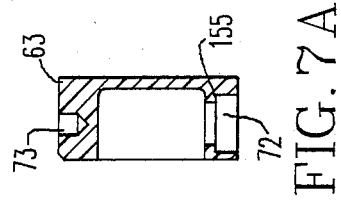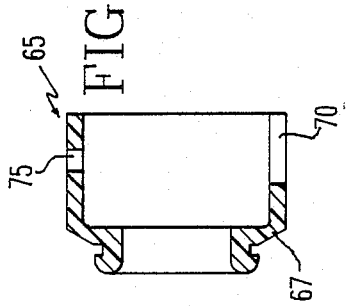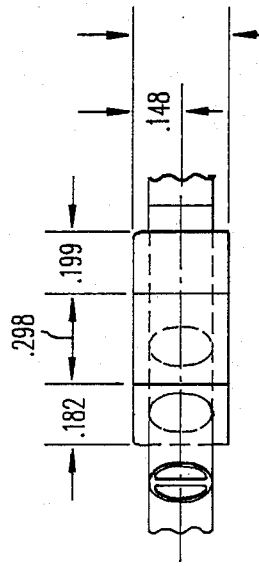

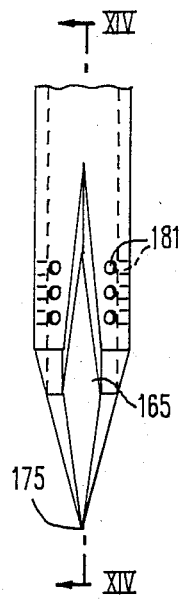
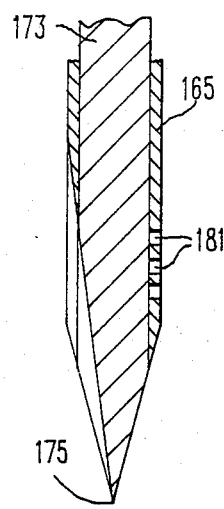
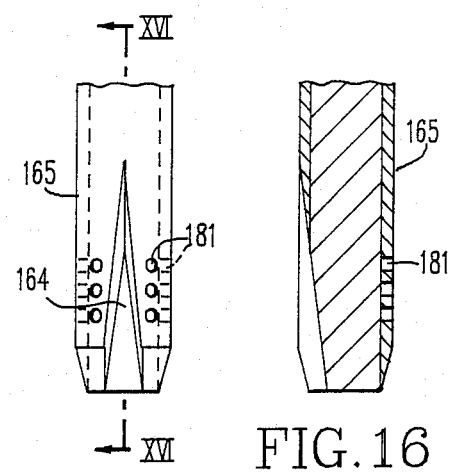
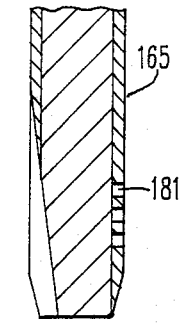
FIG. 13   FIG. 14   FIG. 15   FIG. 16
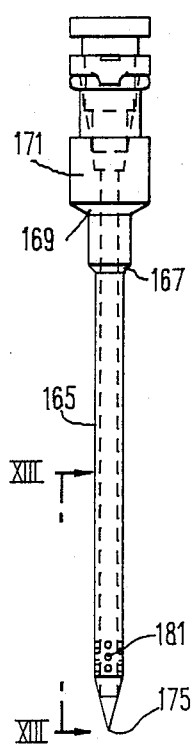
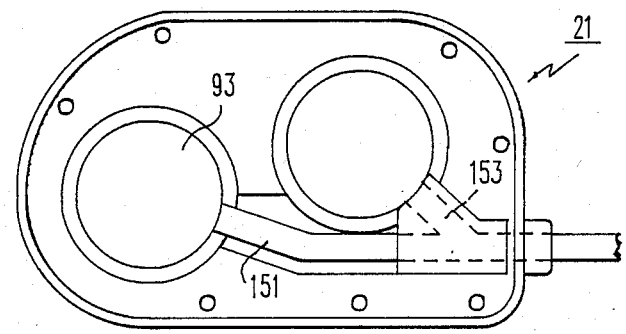
FIG. 12   FIG. 11A

HEMODIALYSIS

BACKGROUND OF THE INVENTION

This invention relates to hemodialysis and it has particular relationship to implantable port assemblies through which toxified blood of a patient is replaced by detoxified blood in the practice of hemodialysis. Notwithstanding that there is substantial demand for implantable hemodialysis apparatus, the availability of such apparatus, in accordance with the teachings of the prior art, is limited. Typically, as disclosed in Shill U.S. Pat. No. 3,791,767, the interchange of detoxified blood for toxified blood is effected through a hypodermic needle which is inserted in a vein (or artery) in the body. An implantable device is disclosed in Constantino U.S. Pat. No. 4,496,350. This device includes a stem which extends outwardly from the body of the host. The patient is subjected to serious inconveniences. For example, the end of the device which extends from the skin must be taped over with great care when the patient is bathing so that water does not penetrate through the joint between its outer surface and the skin. There is also an ever-present danger of infection. In accordance with Constantino's teaching, the flow channels of the device must be spliced into the vein or artery of the patient through which the blood interchange takes place.

It is an object of this invention to overcome the drawbacks and disadvantages of the prior art in the practice of hemodialysis and to provide for the interchange of toxified and detoxified blood of a patient through an implanted hemodialysis port assembly which shall not subject the patient to the inconveniences, hazards and disfigurement involved in the teachings of the prior art.

SUMMARY OF THE INVENTION

In accordance with this invention, there is provided a hemodialysis port assembly including a port and a catheter assembly which are completely implantable. The port assembly includes an inlet septum for passing to the patient detoxified blood from an artificial kidney and an outlet for passing toxified blood to the artificial kidney. The inlet septum is subtended by an inlet plenum and the outlet septum is subtended by an outlet plenum. The catheter assembly includes an inlet channel and an outlet channel. The inlet channel is connected to the inlet plenum and the outlet channel to the outlet plenum. The port is implanted subcutaneously with the septums accessible under the skin of the patient. The catheter assembly extends from the port assembly through the body of the patient and the end of the catheter assembly remote from the port is inserted in a vein in a direction such that detoxified blood from the inlet plenum flows into the vein in the same direction as the normal flow of blood in the vein, while toxified blood is drawn from the vein by the pump of the artificial kidney in a direction opposite to the direction of the normal flow of blood. The inlet channel has a valve at the end of the catheter assembly remote from the port which passes the detoxified blood. The outlet channel has an outlet valve at its end. The outlet valve is displaced from the inlet valve a small, but effective, distance downstream with respect to the flow of toxified blood drawn from the vein through the outlet valve. The outlet valve must be a two-way valve to conduct the blood out to the artifical kidney and, also, to conduct a solution for cleaning the outlet channel. The inlet valve may be a two-way valve to allow cleaning with solution, if needed.

Each valve is a flapper which is hinged at the end of the channel which it terminates. In the standby condition of the hemodialysis port assembly, the valve automatically pivots about the hinge to a closed position closing the valve opening. The blood is incident on each flapper generally perpendicularly to its surface.

In the practice of this invention, the inlet septum is penetrated by a hypodermic needle connected to the detoxified-blood outlet of the artificial kidney and the outlet septum is penetrated by a hypodermic needle connected to the toxified-blood inlet of the artificial kidney. The blood is circulated by the pump of the artificial kidney. Toxified blood is drawn into the artificial kidney from the vein through the outlet valve, outlet channel, outlet plenum, hypodermic needle penetrating the outlet septum. Detoxified blood flows from the artificial kidney, through the hypodermic needle penetrating the inlet septum, the inlet plenum, the inlet channel of the catheter, the inlet valve, the vein into the patient's body. The inflowing or outflowing blood pivots the flapper about its hinge out of the direct path of the blood so that the flow through the valve is substantially unimpeded. Because the inlet and outlet valves are spaced a distance apart longitudinally of the catheter, short circuit flow directly from the inlet channel to the outlet channel is suppressed.

Dialysis can be performed using one port only, by means of or with the assistance of a pump which allows blood to be drawn from the patient to the dialysis machine and thereafter the clean blood back from the dialysis machine to the patient, with the interval needed to clean the blood in between.

BRIEF DESCRIPTION OF THE DRAWINGS

For a better understanding of this invention, both as to its organization and as to its method of operation, together with additional objects and advantages thereof, reference is made to the following description, taken in connection with accompanying drawings, in which:

FIG. 2 is a plan view of an implantable hemodialysis port assembly in accordance with this invention;

FIG. 7 is a fragmental view in longitudinal section showing the manner in which the catheter assembly is connected to the port;

FIG. 7A is a view in transverse section showing a retainer for a septum;

FIG. 7B is a view in transverse section showing a cap for a septum and retainer;

FIG. 8 is a plan view partly in longitudinal section showing the catheter assembly of the implantable hemodialysis port assembly in accordance with this invention;

FIG. 9A is a fragmental view in side elevation taken in the direction IXA—IXA of FIG. 8;

FIG. 11A is a copy of a photograph showing the manner in which the hemodialysis port and the catheter assembly are assembled;

FIG. 12 is a view in side elevation of a typical hypodermic needle used in the practice of this invention;

FIG. 13 is a fragmental view in front elevation taken in the direction XIII—XIII of FIG. 12;

FIG. 14 is a fragmental view in longitudinal section taken along line XIV—XIV of FIG. 13;

FIG. 15 is a fragmental view in front elevation showing the needle with the core pin or stylet removed; and FIG. 16 is a fragmental view in side elevation taken in the direction XVI—XVI of FIG. 15.

FIGS. 8 and 9A shows typical dimensions in inches for a catheter assembly. These dimensions are included for the purpose of aiding those skilled in the art in practicing this invention and not with the intention of limiting this invention in any way.

DETAILED DESCRIPTION OF EMBODIMENT

Figure 1:
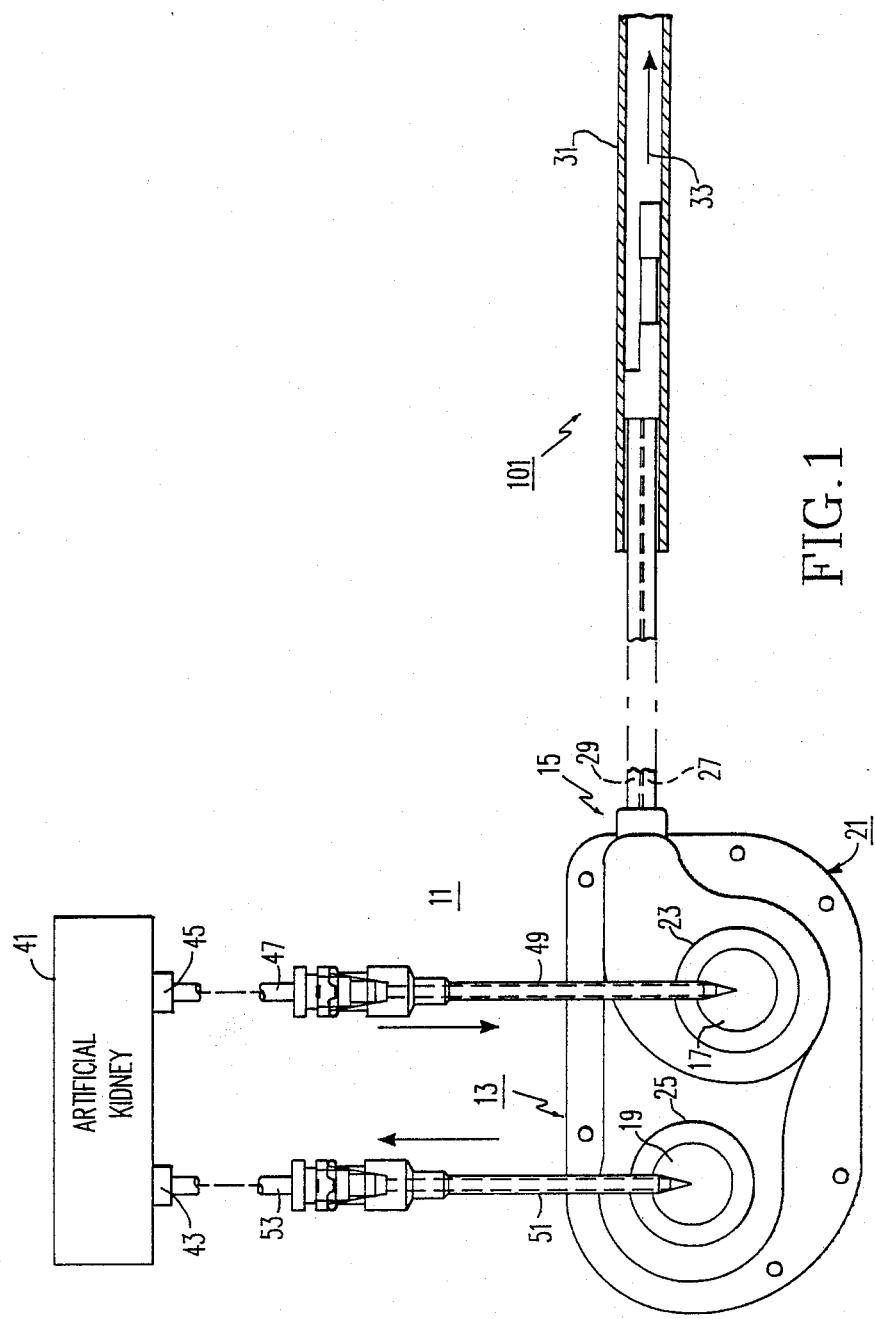
FIG. 1 is a diagrammatic view of hemodialysis apparatus including an implantable hemodialysis port assembly and with which the method according to this invention is practiced.
Figure 4:
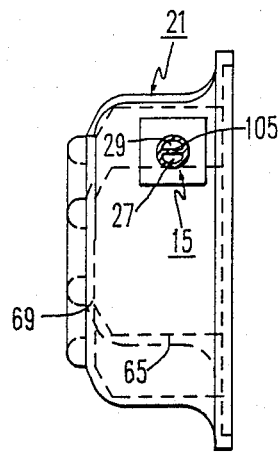
FIG. 4 is a view in end elevation taken in the direction IV—IV of FIG. 2 showing only the port.

The apparatus shown in FIG. 1 includes an implantable hemodialysis port assembly 11 including a port 13 and a catheter assembly 15. The port 13 includes an inlet septum 17 and an outlet septum 19 mounted in a boot 21. The boot has openings 23 and 25 through which the septums 17 and 19 are accessible. The catheter assembly 15 has an inlet channel 27 through which detoxified blood is supplied and an outlet channel 29 through which toxified blood is drawn. The catheter assembly is connected to the port with the inlet channel 27 connected to receive detoxified blood through the inlet septum 17 and the outlet channel 29 connected to receive toxified blood through the outlet septum 19. The port 13 is implanted completely under the skin, typically in the upper chest of a patient. The catheter assembly 15 extends from the port 13 through the body of the patient and its end remote from the port 13 is injected into a vein 31 (or artery) of a patient, typically the subclavian or jugular vein. The normal flow of blood through the vein 31 is in the direction away from the end of the catheter assembly 15 as shown by the arrow 33.

In the practice of this invention, toxified blood of a patient is detoxified by an artifical kidney 41 which has an inlet 43 for receiving toxified blood and an outlet 45 for transmitting detoxified blood. The detoxified blood flows into the inlet channel 27 from the outlet 45 through a conductor 47 which is connected to a hypodermic needle 49 that penetrates the septum 17. The toxified blood is drawn from the outlet channel 29 through a hypodermic needle 51 which is connected to inlet 43 through a conductor 53.

Figure 6:
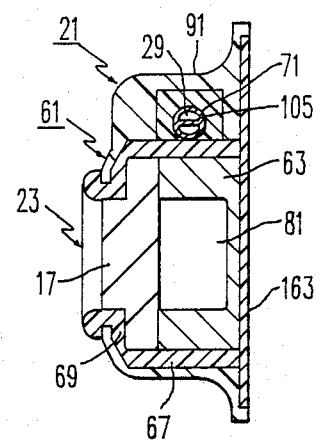
FIG. 6 is a view in transverse section taken along line VI—VI of FIG. 2.
Figure 5:
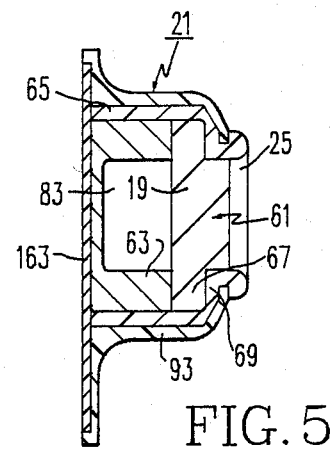
FIG. 5 is a view in transverse section taken along line V—V of FIG. 2.
Figure 3:
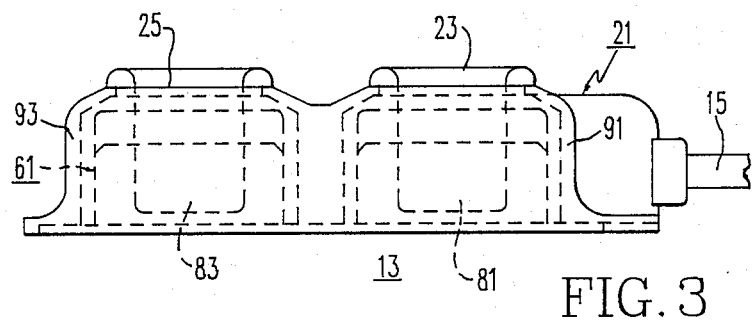
FIG. 3 is a view in side elevation taken in the direction III—III of FIG. 2 showing only the hemodialysis port.

Each septum 17 and 19 has a flanged cylindrical shape (FIGS. 5,6) and is composed typically of Q7-4230 silicone rubber which is biocompatible and is a designation of Dow Corning which is the manufacturer. This material is a soft rubber having a durometer No. 30A. It has high tear strength. In tests the septum of this material was punctured 1100 times before it failed. This is equivalent to seven years of useful life. Each septum 17 and 19 is part of an assembly 61 including a septum retainer 63 and a cap 65 (FIGS. 5,6). The septum retainer 63 is composed of commercially pure titanium and is cup shaped. The septum 17 or 19 is mounted with its flange 67 secured between the upper lip of the retainer and the inner surface of the overhang 69 of the cap. Each retainer 63 has a shouldered opening 72 (FIG. 7) through which the proximal and 71 of each corresponding channel 27 and 29 of the catheter assembly 15 is inserted. Each cap 65 has a slot 70 (FIG. 7B) to accommodate the proximal end of each corresponding channel. After the proximal of each channel 27 and 29 is secured to the retainer 73, the cap 65 is slipped over the proximal end 71 of the channel joined to the septum assembly 61 and the inner end of the slot seats on the end 71. Each retainer has uniformly spaced holes 73 (FIG. 7A) to accommodate positioning pins (not shown) and each cap 65 has corresponding holes 75 (FIG. 7B) to pass the pins.

The septum is sealed pressure tight between the retainer 63 and the cap 65. The cap is composed of polysulfone which is biocompatible. This material is lighter than titanium but hard enough to resist being punctured by a hypodermic needle. The inlet septum 17 is subtended by an inlet plenum 81 in the retainer 63 and the outlet septum 19 by an outlet plenum 83.

The inlet and outlet channels 27 and 29 penetrate into the inlet and outlet plenums 81 and 83 through the holes 69 and the slots 70 in the corresponding retainer 63 and cap 65. The detoxified blood from the input needle 49 is deposited in plenum 81 and drained from this plenum through the inlet channel 27. The toxified blood is deposited in outlet plenum 83 from the outlet channel 29 and is drawn from this plenum by the needle 51.

Figure 10:
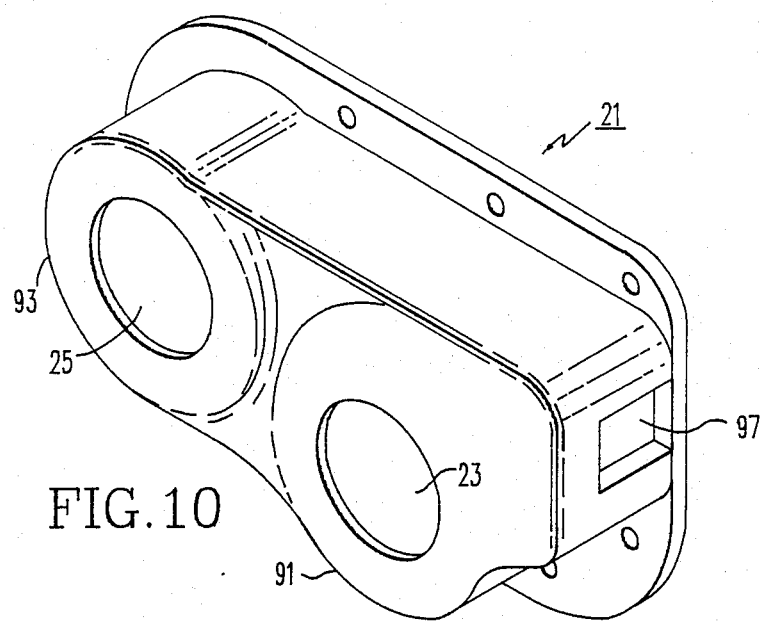
FIG. 10 is a view in isometric showing the boot of the port of the hemodialysis port assembly in accordance with this invention.
Figure 11:
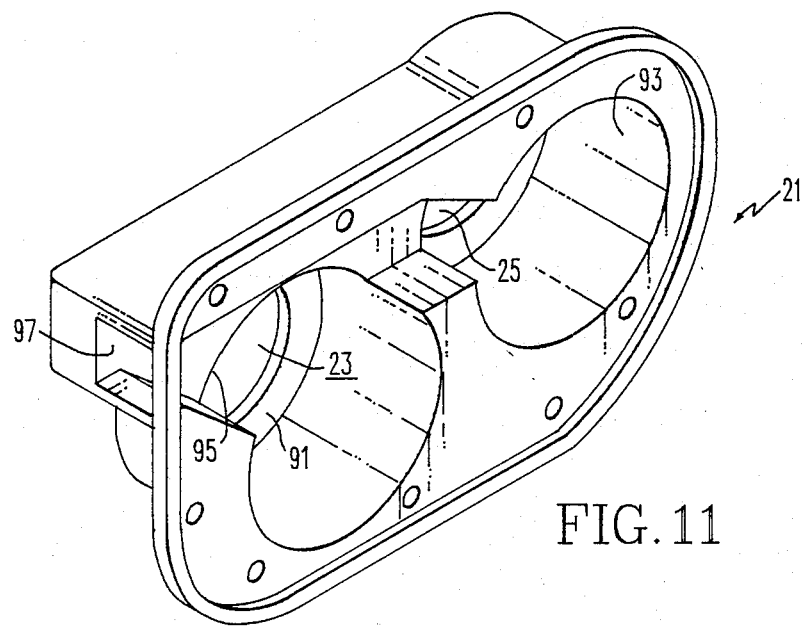
FIG. 11 is a view in isometric showing the interior of this boot.

The septum assemblies 61 containing the inlet septum 17 and the outlet 19 are mounted in pockets 91 and 93 (FIG. 11) of the boot 21 subtended by the holes 23 and 25 respectively (FIGS. 10, 11A). The pockets 91 and 93 have lateral openings which are connected to a slot 95 (FIG. 11) which is in turn connected to a square opening 97 through which the catheter assembly 15 is extended from the interior of the boot 21. The proximal end 71 of the inlet channel 27 of the catheter assembly is positioned along the part of the slot 95 nearest the opening 97 and extends into the assembly 61 containing the inlet septum 17 and the end of the outlet channel 29 extends along the slot 95 to the pocket 93 where it is connected to the assembly 61 containing the outlet septum. The boot 21 is composed of Ticoflex polyurethane sold by Thermedics under the designation EG-80A.-B20. This designation signifies that the material is extrusion grade polyurethane having durometer No. 80A. B-20 means that the material is opaque to X-rays.

The catheter assembly 15 is formed of a long tubular member 101 and a short tubular member 103 (FIGS. 2, 7, 8, 9, 9A) both composed of polyurethane. Each member 101 and 103 initially has a central partition 105 along its length (FIG. 9) dividing each tube into hollow longitudinal or axial sections each of D-shape in transverse cross section. The members 101 and 103 are joined by a Y-connector 107. The assembly of the long and short members 101 and 103 and the Y-connector 107 are formed in a mold. The mold has a solid elbow-shaped core (not shown) having a transverse cross section of the shape of a D that is congruent to the D cross-section of the D-shaped transverse cross section of the channels formed by the partitions 105 in members 101 and 103. The elbow-shaped core is positioned in the mold coextensive with the openings at the ends 109 and 111 of the openings in the long member 101 and the short member 103 which are to form part of the continuous outlet channel 27. The core (not shown) is of yieldable material and extends out of the end 113 of the member 103 so that it may be pulled out. The inlet channel section in member 101 is thus joined to the inlet channel section 103 by the elbow 115. The upper part of the short member 103 terminates at partition 105 as shown at 112 in FIG. 7 and the lower part inwardly of the Y-connector 107 is packed as shown at 114 in FIG. 7. The continuous inlet channel 27 of generally D-shaped cross section is formed of the lower part of the short member 103 and the lower part of member 101 outwardly of the Y-connection and continuous outlet channel 29 is formed of the upper part of member 101 outwardly of the Y-connector and the part of 101 inwardly of the Y-connector. The Y-connector 107 is composed of polyurethane which is similar to the EG-80A-B20, except that it is not extrusion grade and is not opaque to X-rays.

Figure 9E:
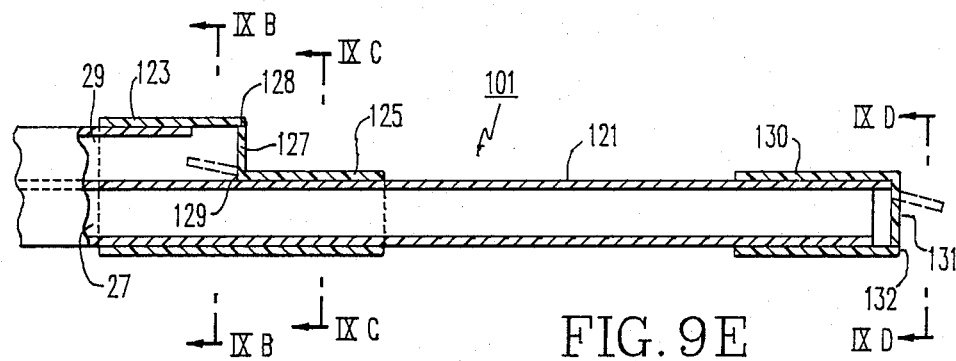
FIG. 9E is a diagrammatic view illustrating the operation of the valves in accordance with this invention for transmitting the blood.
Figure 9:
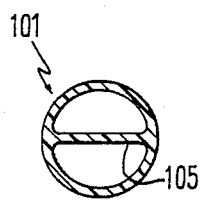
FIG. 9 is a view in transverse section taken in the direction IX—IX of FIG. 8.
Figure 9B:
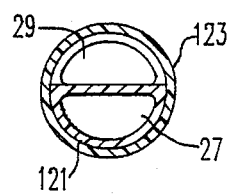
FIG. 9B is a view in transverse section taken along line IXB—IXB of FIG. 8.
Figure 9C:
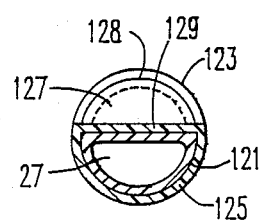
FIG. 9C is a view in transverse section taken along line IXC—IXC of FIG. 8.
Figure 9D:
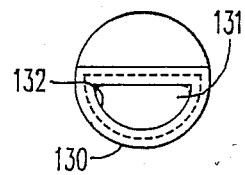
FIG. 9D is a view in end elevation taken in the direction IXD—IXD of FIG. 8.

At its distal end remote from the Y-connector 107, the upper half with reference to FIG. 8 of the tubular member 101 is removed as shown in FIG. 9B so that the catheter assembly 15 terminates in a tube section 121 of generally D-transverse section which constitutes the proximal end of the inlet channel 27. The outermost part of the outlet channel 29 is removed. At the position where the upper half of the member 101 is removed, a boot 123 is mounted. The boot 123 is cylindrical but it has a part 125 of generally D-transverse section which extends a short distance over the section 121. A membrane 127 of generally D-shape is mounted between the bar of the D of part 125 and the upper half 129 of the boot (FIG. 9C). The membrane 127 has a slit 128 along the curved part of the D and constitutes a valve flapper which is pivotal in both directions about its joint 129 to part 125 of the boot. The membrane 127 is the valve for the outlet 29 which permits toxified blood to flow out or cleaning solution to flow in.

On the end of section 121, another boot 130 is mounted. This boot is of generally D-transverse section and its end is closed by a membrane 131 of D-shape. The membrane has a slit 132 along the curved part of the D and constitutes a valve flapper which is pivoted on the bar of the D of the section 121. The membrane 131 constitutes a two-way valve for the inlet of detoxified blood.

The valves 127 and 131 are capable of handling the high flow of the blood which is carried by the catheter. Typically, the rate of flow is 200 to 400 cubic centimeters per minute. The operation of the valve is illustrated in FIG. 9E. The standby position is shown in full lines and the operating position with toxified blood flowing in is shown in broken lines. It is seen that the valve 127 is thrust downwardly providing a substantially open channel for the blood. Valve 131 operates in the same way.

The boots 123 and 130 are composed of Ticoflex EG-80A. The membranes 131 are also composed of the same material and have a thickness of about 0.010-inch. This material is flexible so that the valve flappers 127 and 131 automatically reset to the closed position in the standby condition of the hemodialysis port assembly.

Near their proximal ends inwardly of the neck 117 of the Y-connector 107, each member 101 and 103 is provided with a ring 141 (FIG. 8) of polyurethane EG-80A or EG-80A-B20. The ring is secured to each member by an adhesive typically consisting of a solution of 15% polyurethane in dimethylacetamide (DMA). A sleeve 143 (FIG. 7) of commercially pure titanium abuts each ring 141. The rings 141 are each packed with adhesive so that the rings and sleeves are secured in the shouldered opening 72 in retainer 63 when the adhesive sets. The sleeves are spot welded to the retainer 63. The rings 141 and the sleeves 143 are mounted on the members 101 and 103 before the Y-connector 107 is molded to the members or the rings and sleeves may be mounted after the Y-connector is molded. A plug 145 of polyurethane is secured in the channel 27 of member 101 between the end where the ring 141 and sleeve 143 are secured and the Y-connector 107. A plug 147 is secured in the channel 29 of the member 103 between its end where the ring and sleeve are secured and the Y-connector (FIG. 7). These plugs confine the inflow of detoxified blood to the inlet channel 27 and the outflow of toxified blood to the outlet channel 29.

The surface of the Y-connector 107 is shaped so that it seats in slot 95 (FIG. 11) of the boot 21. The neck 117 of the Y-connector is of square cross section and is dimensioned so that it is tightly engaged by the boundaries of hole 97. In the construction of the hemodialysis port assembly 11, the inlet and outlet septums are secured between the associated retainers 63 and caps 65 and positioning pins (not shown) are inserted in holes 73 and 75 (FIG. 7A, 7B). The respective inlet and outlet assemblies are thus formed. The branches 151 and 153 (FIGS. 2, 7, 11A) of the members 101 and 103 which extend from the Y-connector 107 are engaged at their respective ends in the holes 72 (FIG. 7A) of the retainers 63 with the rings 141 engaging the shoulders 155 (FIG. 7A). The branch 101 is pulled through the square hole 97 so as to cause the neck 117 to nest in hole 97. The branches 151 and 153 are then nested in slot 97 and the inlet septum assembly 61 is seated in pocket 91 and the outlet septum assembly 61 in pocket 93 (FIG. 1). The boot 21 is then positioned with its open bottom upwardly and liquid polyurethane, Ticoflex 2-80A, is deposited in the boot. When this polyurethane solidifies, it forms a matrix 161 (FIG. 7) in which the assemblies 61 and the branches 151 and 153 are enclosed. The boot 21 is then sealed by the cover 163 (FIGS. 5 and 6) which is composed of polyurethane EG-80A-B20.

The inlet and outlet hypodermic needles 49 and 51 used in the practice of this invention are of the type having a lateral opening 164 (FIGS. 12–16). Each needle includes a hollow cylindrical outer shell 165 which is of increasing diameter at the upper end with reference to FIG. 12 in steps separated by tapered shoulders 167 and 169. The upper end 171 carries a Luer lock fitting which is structured to engage a male fitting (not shown) at the end of conductors 47 and 53 (FIG. 1). A removable core pin 173 having a sharp tip 175 extends through the shell 165 projecting below the opening 163 as shown in FIG. 14. The core pin 173 is a snug fit in the shell 163.

In the practice of this invention, the hemodialysis port assembly 11 is implanted with the port subcutaneous and the septums 17 and 19 accessible. In use, the skin covering the port and each septum is penetrated by the hypodermic needles 49 and 51 with the sharp core pin 173 serving to produce the penetration. The core pin 173 is then removed and the conductors 47 and 53 from the artificial kidney 41 are connected to the needles by means of the Luer fittings. The interchange of blood then proceeds when the artificial kidney is enabled. Holes 181 can be provided in the walls of shell 165 to facilitate the flow of blood into or out of the needles. In this application and in the claims the words "distal" and "proximal" are used. As used in this application, the word "distal" means near or at the blood vessel where the catheter is injected and the word "proximal" means remote from the blood vessel where the catheter is injected. The distal end of the catheter is at the valves 127 and 131 (FIG. 9E); the proximal end of the catheter is at the port 13. The above definitions of "distal" and "proximal" are the same as in Bates U.S. Pat. No. 4,643,711, but are the opposite of Groshong U.S. Pat. No. 4,549,879.

While an embodiment of this invention and practice of this invention are disclosed herein, many modifications thereof are feasible. This invention is not to be restricted except insofar as is necessitated by the spirit of the prior art.

We claim:

1. A hemodialysis port assembly including a port structured for complete subcutaneous implantation in a patient, septum means in said port, an inlet hypodermic needle and an outlet hypodermic needle to penetrate said septum means, said port assembly also including a catheter assembly connected to said septum means, said catheter assembly to be implanted in said patient with its distal end injected into a blood vessel of said patient, said catheter assembly including a first channel, to to connected to said inlet needle to pass detoxified blood from said inlet needle to said blood vessel, and a second channel conducting fluid separately from said first channel, to be connected to said outlet needle, to pass toxified blood from said blood vessel to said outlet needle, said first channel and said second channel being structured in said catheter so as to permit both said channels to be injected into a common blood vessel in transmission communication with the blood in said blood vessel, and valve means connected to each said channel for gating the flow of detoxified blood into said blood vessel and toxified blood out of said blood vessel.

2. The hemodialysis port assembly of claim 1 wherein the separate channel means includes means for substantially suppressing circulation of detoxified blood in a short circuit including said inlet needle, said first channel, said second channel, and said outlet needle.

3. The hemodialysis port assembly of claim 1 characterized by that the cross-sectional area of the first channel through which the detoxified blood or fluid is conducted is substantially equal to the cross-sectional area of the second channel through which the toxified blood or fluid is conducted.

4. The hemodialysis port assembly of claim 1 characterized by that the cross-sectional area of the first channel through which the detoxified blood is conducted and the cross-sectional area of the second channel through which the toxified blood is conducted are of relatively large magnitude to preclude the development of relatively large pressure heads in said first channel or said second channel to drive said detoxified or toxified blood respectively through said first channel or said second channel respectively and resulting destruction of detoxified or toxified blood cells respectively.

5. A hemodialysis port assembly including a port assembly structured for complete subcutaneous implantation in a patient, said port assembly including an inlet septum and an inlet plenum in communication with said inlet septum, said inlet septum to be penetrated by an inlet hypodermic needle for the delivery of detoxified blood to said inlet plenum, said port assembly also including an outlet septum and an outlet plenum in communication with said outlet septum, said outlet plenum to be penetrated by an outlet hypodermic needle for transmission of said patient's toxified blood from said outlet plenum, a catheter assembly to be implanted in said patient, said catheter assembly including an inlet to be connected between said inlet plenum and a blood vessel of said patient with its distal end to be injected in said blood vessel for transmission of detoxified blood from said inlet plenum to said blood vessel, and an outlet channel, separate from said inlet channel, to be connected between said outlet plenum and said blood vessel with its distal end also to be injected in said blood vessel for transmission of toxified blood from said blood vessel to said outlet plenum, and valve means connected to each said channel for gating the flow of detoxified blood from said inlet channel into said blood vessel and toxified blood from said blood vessel into said outlet channel.

6. A hemodialysis port assembly including a port and a catheter assembly connected to said port, said port and catheter assembly being structured for complete implantation in a patient with said port implanted subcutaneously and said catheter assembly implanted between said port and the vascular system of said patient, said port including an inlet septum and an inlet plenum connected to said inlet plenum, and an outlet septum and an outlet plenum connected to said outlet septum, said inlet septum to be penetrated by an inlet hypodermic needle for delivery of detoxified blood to said inlet plenum and said outlet septum to be penetrated by an outlet hypodermic needle for transmission of toxified blood from said outlet septum, said catheter assembly including an inlet channel connected to said inlet septum and to be connected to said vascular system for transmission of detoxified blood from said inlet plenum to said vascular system, and an outlet channel separate from said inlet channel connected to said outlet plenum and to be connected to said vascular system for transmission of toxified blood from said vascular system to said outlet plenum, said inlet channel and said outlet channel being combined into a physically integral unit capable of being inserted into a common blood vessel of the patient's vascular system, and valve means in said inlet channel and said outlet channel actuable to permit the flow of detoxified blood to the vascular system or toxified blood from the vascular system.

7. The hemodialysis port assembly of claim 6 wherein the catheter assembly includes means for substantially suppressing circulation of detoxified blood in the short circuit including said inlet septum, said inlet channel, said outlet channel and said outlet septum.

8. The hemodialysis port assembly of claim 6 wherein, to suppress substantially circulation of blood in the short circuit including the inlet plenum, the inlet channel, the outlet channel and the outlet plenum, the outlet valve is spaced from the inlet valve along the catheter with the outlet valve more remote from the distal end of the catheter.

9. The hemodialysis port assembly of claim 6 wherein at least the outlet valve is a two-way valve.

10. The hemodialysis port assembly of claim 1 wherein the first and second channels each terminates in a flapper valve having a flapper mounted pivotally at the distal end of its associated channel, each said flapper being mounted in its associated channel in a position such that blood or other fluid which is to flow into or out of the associated channel, as the case may be, is incident on the flapper generally perpendicularly to its surface and will exert pressure to pivot said each associated flapper from a standby closed position out of the path of the flowing blood or other fluid so that the flow is substantially unimpeded, the pivotal mounting said each flapper being resilient so that on the relaxation of the associated said pressure, said each flapper returns to the standby closed position.

11. A hemodialysis port assembly including a port structure for complete subcutaneous implantation in a patient, septum means in said port structure, an inlet hypodermic needle and an outlet hypodermic needle to penetrate said septum means, said hemodialysis port assembly also including a catheter assembly connected to said septum means, said catheter assembly to be implanted in said patient connected to the vascular system of said patient, said catheter assembly including an inlet channel, to be connected to said inlet needle, to pass detoxified blood from said inlet needle to said vascular system, and an outlet channel separate from said inlet channel, to be connected to said outlet needle, to pass toxified blood from said vascular system to said outlet needle, one of said channels extending beyond the distal end of said other channel a predetermined distance, a first flapper valve connected to the distal end of said inlet channel, said first valve having a flapper for closing and opening said valve, the surface of said flapper being generally perpendicular to the axis of said channel, and a second flapper valve connected to the distal end of said outlet channel, said second valve having a flapper for closing and opening said second valve, the surface of said flapper being generally perpendicular to the axis of said outlet channel, the said distance being of such length that short-circuit flow between said inlet channel and said outlet channel is suppressed.

12. The hemodialysis port assembly of claim 11 wherein the one channel whose distal end extends beyond the end of the other channel is the inlet channel and the other channel is the outlet channel.

13. The hemodialysis port assembly of claim 5 characterized by valve means including an inlet valve terminating the distal end of the inlet channel and an outlet valve terminating the distal end of the outlet channel, said inlet valve when open to conduct detoxified blood to the blood vessel and said outlet valve when open to conduct toxified blood from the blood vessel, each said valve having a flapper, the surface of each said flapper being generally perpendicular to the axis of its associated channel, each said flapper being pivotally mounted to set its associated valve in closed position in the absence of flow of blood or other fluid and to be pivoted to the open position under the force of the flow of blood or other fluid and to return resiliently to the closed position on relaxation of said force.

14. The method of conducting hemodialysis on a patinet with an artificial kidney and a hemodialysis port assembly including a port and a catheter assembly having separate inlet and outlet branches connected to said port and with inlet and outlet hypodermic needles; the said method comprising: implanting said hemodialysis port assembly in said patient with said port implanted subcutaneously in a region of the patient's body which is accessible to said needles and said catheter assembly implanted connected to said port and to a blood vessel of said patient at a place upstream with respect to the normal flow of the blood of said patient through said blood vessel, both said inlet and said outlet branches being connected to said blood vessel, inserting the outlet needle in said port and transmitting the toxified blood from said patient through an outlet opening in said outlet branch and said outlet needle transmitting toxified blood into said artificial kidney, said toxified blood being transmitted in the direction opposite to the direction of the direction of normal flow of blood through said blood vessel, detoxifying said toxified blood derived from said outlet needle in said artificial kidney, inserting said inlet needle into said port and through said inlet needle and said inlet branch supplying detoxified blood from said artificial kidney to said blood vessel through an inlet opening in said inlet branch, said detoxified blood as it is supplied being transmitted in the same direction as the normal flow of blood through said blood vessel, said outlet opening in said outlet branch being displaced along said catheter assembly from said inlet opening in said inlet branch an effective distance along said catheter assembly to suppress substantially the circulation of blood undesirably through the short circuit including said inlet needle, said inlet branch, said outlet branch and said outlet needle.

15. The method of claim 14 wherein the port is implanted subcutaneously in the chest and the channel means is inserted in the subclavian vein.

16. The method of claim 14 practiced with a catheter assembly whose inlet and outlet branches each has a valve near its distal end, each said valve being closed in the standby condition of said hemodialysis port assembly; the said method including, in the transmission of the toxified blood to the blood vessel through the outlet branch, causing the pressure of the toxified blood to open the associated valve and, in the transmission of the detoxified blood from the blood vessel through the outlet branch, causing the pressure of the detoxified blood to open the associated valve.

17. The method of conducting hemodialysis on a patient with an artificial kidney and a hemodialysis port assembly including a port having an inlet septum and an inlet plenum, an outlet septum and an outlet plenum and a catheter having an inlet conductor and an outlet conductor, each conductor having a valve at its distal end, each said valve being closed in standby condition of said hemodialysis port assembly, the said method including implanting said hemodialysis port assembly in said patient with said port implanted subcutaneously with said septums accessible to injection of hypodermic needles and said conductors injected together in a blood vessel of said patient, and circulating blood through said port assembly with the toxified blood of said patient flowing into said artificial kidney from said blood vessel through its associated valve, said toxified blood opening said valve under its pressure and through said outlet conductor, said outlet plenum and said outlet septum, and detoxified blood flowing from said kidney into said blood vessel through said inlet septum, said inlet plenum, said inlet conductor and its associated valve, opening said inlet valve, said toxified blood opening, said last-named valve under its pressure.

* * * * *